US009078819B2

(12) United States Patent
Oyama

(10) Patent No.: US 9,078,819 B2
(45) Date of Patent: *Jul. 14, 2015

(54) COSMETIC TRANSPARENT GEL PREPARATION AND GELLING AGENT

(71) Applicant: The Nisshin OilliO Group, Ltd., Tokyo (JP)

(72) Inventor: Keiichi Oyama, Yokohama (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 39 days.

This patent is subject to a terminal disclaimer.

(21) Appl. No.: 14/083,820

(22) Filed: Nov. 19, 2013

(65) Prior Publication Data

US 2015/0087726 A1    Mar. 26, 2015

Related U.S. Application Data

(63) Continuation of application No. 13/062,890, filed as application No. PCT/JP2009/004542 on Sep. 11, 2009, now Pat. No. 8,597,669.

(30) Foreign Application Priority Data

Sep. 12, 2008  (JP) .................................. 2008-235068

(51) Int. Cl.
| | |
|---|---|
| *A61K 8/04* | (2006.01) |
| *A61K 8/365* | (2006.01) |
| *A61K 8/37* | (2006.01) |
| *A61K 8/891* | (2006.01) |
| *A61Q 19/00* | (2006.01) |

(52) U.S. Cl.
CPC ............... *A61K 8/042* (2013.01); *A61K 8/365* (2013.01); *A61K 8/37* (2013.01); *A61K 8/375* (2013.01); *A61K 8/891* (2013.01); *A61Q 19/00* (2013.01); *A61K 2800/262* (2013.01)

(58) Field of Classification Search
None
See application file for complete search history.

(56) References Cited

U.S. PATENT DOCUMENTS

| 5,106,625 | A | 4/1992 | Yamamoto et al. |
| 2006/0051307 | A1 | 3/2006 | Gotou et al. |
| 2007/0190002 | A1 | 8/2007 | Gotou et al. |

FOREIGN PATENT DOCUMENTS

| EP | 1466586 | A1 | 10/2004 |
| EP | 1614411 | A1 | 1/2006 |
| EP | 1857092 | A1 | 11/2007 |
| JP | 07-126604 | | 5/1995 |
| JP | 2000-204016 | | 7/2000 |
| JP | 2001-039817 | | 2/2001 |
| JP | 2008-031102 | | 2/2008 |
| WO | 2004100902 | A1 | 11/2004 |
| WO | 2008013107 | A1 | 1/2008 |

OTHER PUBLICATIONS

Database GNPD [Online] MINTEL; Nov. 30, 2006, Pop Beauty: "Naturally Popette Face Palette", XP-002719917, Database accession No. 612028.
Database GNPD [Online] MINTEL; Jun. 30, 2008 (Jun. 30, 2006), Estee Lauder: "Hydra Lustre Lipstick", XP-002719916, Database accession No. 951153.
European Search Report for Application No. 09812918.2, mailed Feb. 24, 2014.
Tracy Strilich, GRAS notice #203, submitted to FDA May 26, 2006, http://www.accessdata.fda.gov/scripts/fcn/gras_notices/612849A.PDF.
Search Report and Written Opinion from ISA for PCT Application No. PCT/JP2009/004542, Nov. 2, 2009, 9 pp.
U.S. Patent and Trademark Office, Office Action issued in U.S. Appl. No. 13/062,890, mailed Nov. 16, 2012, 23 pp.
U.S. Patent and Trademark Office, Notice of Allowance issued in U.S. Appl. No. 13/062,890, mailed Aug. 20, 2013, 11 pp.
Tracy Strilich, GRAS notice #203, submitted to FDA May 26, 2006, http:www/accessdata.fda/gov/scripts/fcn/gras_notices/612849A.PDF.

*Primary Examiner* — Misook Yu
*Assistant Examiner* — Kauser M Akhoon
(74) *Attorney, Agent, or Firm* — Wood, Herron & Evans, LLP

(57) ABSTRACT

A cosmetic transparent gel preparation that has high levels of transparency and hardness and favorable usability, as well as a gelling agent that is ideal for use in the cosmetic transparent gel preparation. The cosmetic transparent gel preparation contains an esterification reaction product obtained by reacting glycerol with a dibasic acid of 18 to 28 carbon atoms and a fatty acid of 8 to 28 carbon atoms (excluding dibasic acids), 12-hydroxystearic acid, and an oil component. The gelling agent contains an esterification reaction product obtained by reacting glycerol with a dibasic acid of 18 to 28 carbon atoms and a fatty acid of 8 to 28 carbon atoms (excluding dibasic acids), and 12-hydroxystearic acid.

15 Claims, No Drawings dropped# COSMETIC TRANSPARENT GEL PREPARATION AND GELLING AGENT

TECHNICAL FIELD

The present invention relates to a cosmetic transparent gel preparation that exhibits excellent transparency and hardness and extremely favorable usability, and also relates to a gelling agent that is ideal for use in the cosmetic transparent gel preparation.

Priority is claimed on Japanese Patent Application No. 2008-235068, filed Sep. 12, 2008, the content of which is incorporated herein by reference.

BACKGROUND ART

Oil-based transparent cosmetic preparations mainly offer advantages such as a beautiful external appearance and a transparent-like finish when applied. A large variety of bases have been investigated for such preparations, and of these, numerous investigations have been conducted of bases containing 12-hydroxystearic acid.

For example, a transparent cosmetic preparation containing 12-hydroxystearic acid, a cellulose derivative and an oil component (see Patent Document 1), and a transparent cosmetic preparation containing 12-hydroxystearic acid, a dextrin fatty acid ester and an oil component (see Patent Document 2) have previously been disclosed. These preparations are claimed to address usage problems and transparency problems associated with conventional transparent cosmetic preparations such as poor spreadability, a tendency to come off during application, an unsatisfactory finish following application, and a deterioration in the transparency over time.

On the other hand, transparent cosmetic preparations frequently contain a gelling agent for the oil-based component, and examples of gelling agents that have already been disclosed include compositions corresponding with esterification reaction products obtained by reacting glycerol with a dibasic acid of 18 to 28 carbon atoms and a fatty acid of 8 to 28 carbon atoms (see Patent Documents 3 and 4).

PRIOR ART DOCUMENTS

Patent Documents

[Patent Document 1]
Japanese Laid-Open Patent Application No. 2000-204016
[Patent Document 2]
Japanese Laid-Open Patent Application No. 2001-39817
[Patent Document 3]
Japanese Laid-Open Patent Application No. Hei 07-126604
[Patent Document 4]
Japanese Laid-Open Patent Application No. 2008-31102

DISCLOSURE OF INVENTION

Problems to be Solved by the Invention

However, with the transparent cosmetic preparations disclosed in Patent Documents 1 and 2, a problem has existed in that when the cellulose derivative or dextrin fatty acid ester is added to the 12-hydroxystearic acid, the mixture must be heated at a high temperature of 95° C. or higher to achieve dissolution, which can have an adverse effect on the quality of the transparent cosmetic preparation. In particular, because an accurate temperature setting cannot be achieved with a water bath, heating with steam or a heater has been necessary, but these heating methods increase the likelihood of localized heating, increasing the chances of adverse effects on the quality of the oil-based component. Moreover, the transparent cosmetic preparations disclosed in Patent Documents 1 and 2 both suffer from low levels of hardness.

Further, even if the gelling agent disclosed in Patent Document 3 is added to an oil component, a transparent preparation is not obtained, whereas when the gelling agent disclosed in Patent Document 4 is added to an oil component, although transparency is achieved, the hardness level is low. Accordingly, with either gelling agent, obtaining a cosmetic transparent gel preparation having high levels of transparency and hardness and favorable usability has proven impossible.

The present invention takes the above circumstances into consideration, with an object of providing a cosmetic transparent gel preparation that has high levels of transparency and hardness and favorable usability, as well as a gelling agent that is ideal for use in the cosmetic transparent gel preparation.

Means to Solve the Problems

As a result of intensive research aimed at achieving the above object, the inventors of the present invention discovered that, totally unexpectedly, a cosmetic preparation containing an esterification reaction product obtained by reacting glycerol with a dibasic acid of 18 to 28 carbon atoms and a fatty acid of 8 to 28 carbon atoms, in combination with 12-hydroxystearic acid and an oil component was able to achieve the above object, and they were therefore able to complete the present invention.

In other words, in order to achieve the object described above, the present invention provides a cosmetic transparent gel preparation containing an esterification reaction product obtained by reacting glycerol with a dibasic acid of 18 to 28 carbon atoms and a fatty acid of 8 to 28 carbon atoms (excluding dibasic acids), 12-hydroxystearic acid and an oil component.

The cosmetic transparent gel preparation of the present invention preferably contains 4 to 20% by mass of the 12-hydroxystearic acid and 1 to 15% by mass of the esterification reaction product.

Further, in the cosmetic transparent gel preparation of the present invention, the mass ratio between the 12-hydroxystearic acid and the esterification reaction product is preferably within a range from 20:1 to 1:2.

Furthermore, the cosmetic transparent gel preparation of the present invention preferably contains, as the oil component, not less than 20% by mass of an ester oil that has a hydroxyl value of 40 to 300 and is a liquid at normal temperature.

The present invention also provides a gelling agent containing an esterification reaction product obtained by reacting glycerol with a dibasic acid of 18 to 28 carbon atoms and a fatty acid of 8 to 28 carbon atoms (excluding dibasic acids), and 12-hydroxystearic acid.

The present invention also provides a cosmetic transparent gel preparation containing the gelling agent of the present invention and an oil component.

Effect of the Invention

The present invention is able to provide a cosmetic transparent gel preparation that has high levels of transparency and hardness, and favorable usability.

BEST MODE FOR CARRYING OUT THE INVENTION

A more detailed description of the present invention is presented below.

A cosmetic transparent gel preparation of the present invention contains an esterification reaction product obtained by reacting glycerol, a dibasic acid of 18 to 28 carbon atoms and a fatty acid of 8 to 28 carbon atoms (excluding dibasic acids), 12-hydroxystearic acid, and an oil component.

As mentioned above, a transparent cosmetic preparation disclosed in Japanese Laid-Open Patent Application No. 2000-204016 contains 12-hydroxystearic acid, a cellulose derivative and an oil component, and a transparent cosmetic preparation disclosed in Japanese Laid-Open Patent Application No. 2001-39817 contains 12-hydroxystearic acid, a dextrin fatty acid ester and an oil component, but both of these preparations have low levels of hardness. Furthermore, the gelling agent disclosed in Japanese Laid-Open Patent Application No. 2008-31102 contains an esterification reaction product obtained by reacting glycerol, a dibasic acid of 18 to 28 carbon atoms and a fatty acid of 8 to 28 carbon atoms, but even if this gelling agent is blended with an oil component, the resulting preparation has a low level of hardness. Accordingly, even if the esterification reaction product contained within the above gelling agent were to be used instead of the cellulose derivative or dextrin fatty acid ester in the transparent cosmetic preparations described above, thereby forming a similar configuration to the cosmetic transparent gel preparation of the present invention, it would not normally be thought that the hardness of the resulting transparent cosmetic preparation would increase. Furthermore, when a similar gelling agent disclosed in Japanese Laid-Open Patent Application No. Hei 07-126604 is blended with an oil component, the resulting blended mixture is not transparent, and therefore even if the esterification reaction product contained within the above gelling agent were to be used instead of the cellulose derivative or dextrin fatty acid ester in the transparent cosmetic preparations described above, it is difficult to imagine that the resulting cosmetic preparation would be transparent.

However, against all such expectations, the cosmetic transparent gel preparation of the present invention unexpectedly exhibited high levels of transparency and hardness, as well as favorable usability.

The components used in the present invention are described below in detail.

The 12-hydroxystearic acid may be a commercially available material, or may be chemically synthesized. Further, 12-hydroxystearic acid obtained by performing a chemical treatment on a specific raw material may also be used, and examples of such materials include a material obtained by hydrogenating ricinoleic acid, and a material obtained by hydrolyzing hydrogenated castor oil.

The amount added of the 12-hydroxystearic acid may be adjusted appropriately in accordance with factors such as the intended use of the target cosmetic transparent gel preparation, but usually, is preferably within a range from 4 to 20% by mass, more preferably from 6 to 19% by mass, and still more preferably from 7 to 12% by mass, relative to the total mass of all the components.

The dibasic acid of 18 to 28 carbon atoms is preferably a linear or branched chain, and is preferably a saturated dibasic acid. Specific examples include dicarboxylic acids of 18 to 28 carbon atoms. Of these, dibasic acids of 18 to 20 carbon atoms are preferred, including octadecanedioic acid, nonadecanedioic acid and eicosanedioic acid.

Further, the dibasic acid of 18 to 28 carbon atoms may be either a single compound or a mixture of two or more compounds. In the case of a mixture of two or more compounds, the combination used and the ratio between the compounds may be selected appropriately in accordance with the intended purpose.

The fatty acid of 8 to 28 carbon atoms is a fatty acid that is not a dibasic acid, may be either a linear or branched chain, preferably contains from 8 to 22 carbon atoms, and most preferably contains 20 carbon atoms. A saturated fatty acid is preferred. Specific examples include caprylic acid, capric acid, lauric acid, myristic acid, palmitic acid, stearic acid, behenic acid, oleic acid, ricinoleic acid, palmitoleic acid, isooctanoic acid (such as 2-ethylhexanoic acid), isononanoic acid (such as 3,5,5-trimethylhexanoic acid), isopalmitic acid, isostearic acid (such as 2-heptylundecanoic acid and multimethyl branched isostearic acid manufactured by Emery Oleochemicals Group), isoeicosanoic acid, cerotic acid, montanic acid, melissic acid and the like. Of these, from the viewpoint of achieving a favorable gelling capability relative to the oil component, behenic acid is particularly preferred.

Furthermore, the fatty acid of 8 to 28 carbon atoms may be either a single compound or a mixture of two or more compounds. In the case of a mixture of two or more compounds, the combination used and the ratio between the compounds may be selected appropriately in accordance with the intended purpose.

The esterification reaction product in the present invention has a hydroxyl value that is preferably not more than 40, more preferably not more than 35, and still more preferably 30 or less. Provided the hydroxyl value of the esterification reaction product satisfies the above range, the transparent sensation and gel-forming ability of the gelling agent can both be further improved. In this description, the "hydroxyl value" refers to the value obtained using the hydroxyl value measurement method prescribed in the general test methods of the Japanese Standards for Cosmetic Ingredients.

The esterification reaction product used in the present invention may be a commercially available product, or may be chemically synthesized.

Examples of preferred commercially available products include glyceryl (behenate/isostearate/eicosanedioate) (product name: NOMCORT SG, manufactured by Nisshin Oillio Group) and glyceryl (behenate/eicosanedioate) (product name: NOMCORT HK-G, manufactured by Nisshin Oillio Group).

In those cases where the esterification reaction product is chemically synthesized, a product obtained by using a conventional method to perform an esterification reaction using the desired dibasic acid of 18 to 28 carbon atoms, fatty acid of 8 to 28 carbon atoms (excluding dibasic acids) and glycerol as raw materials may be used.

The amount added of the esterification reaction product in the present invention may be adjusted appropriately in accordance with factors such as the intended use of the target cosmetic transparent gel preparation, but usually, is preferably within a range from 1 to 15% by mass, and more preferably from 1 to 12% by mass, relative to the total mass of all the components.

Further, the esterification reaction product may be either a single product or a mixture of two or more products. In the case of a mixture of two or more products, the combination used and the ratio between the products may be selected appropriately in accordance with the intended purpose.

The mass ratio between the 12-hydroxystearic acid and the esterification reaction product of the present invention (namely the mass ratio of 12-hydroxystearic acid: esterification reaction product of the present invention) is preferably within a range from 20:1 to 1:2, more preferably from 10:1 to 1:1, still more preferably from 5:1 to 1:1, and still more preferably from 5:1 to 2:1.

There are no particular limitations on the oil component, provided addition of the oil component yields a transparent cosmetic preparation, and any of the types of oil components used in typical cosmetic preparations may be used. Examples include liquid oils and fats, solid oils and fats, waxes, hydrocarbon oils, higher fatty acids, higher alcohols, synthetic ester oils, natural ester oils and silicone oils. More specific examples are listed below.

Examples of the liquid oils and fats include avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice germ oil, tung oil, Japanese tung oil, jojoba oil, germ oil, triglycerol, glycerol trioctanoate, glycerol triisopalmitate and the like.

Examples of the solid oils and fats include cacao fat, coconut oil, horse tallow, hardened coconut oil, palm oil, beef tallow, sheep tallow, hardened beef tallow, palm kernel oil, lard, beef bone tallow, Japan kernel oil, hardened oil, beef leg tallow, Japan wax, hardened castor oil and the like.

Examples of the waxes include beeswax, candelilla wax, cotton wax, carnauba wax, bayberry wax, Ericerus Pela wax, spermaceti, montan wax, bran wax, lanolin, kapok wax, lanolin acetate, liquid lanolin, sugar cane wax, isopropyl lanolate, hexyl laurate, reduced lanolin, jojoba wax, hardened lanolin, shellac wax, POE lanolin alcohol ether, POE lanolin alcohol acetate, POE cholesterol ether, polyethylene glycol lanolate, POE hydrogenated lanolin alcohol ether and the like.

Examples of the hydrocarbon oils include liquid paraffin, isoparaffin, ozokerite, squalane, pristane, ceresin, squalene, Vaseline, microcrystalline wax, paraffin wax, α-olefin oligomers and the like.

Examples of the higher fatty acids include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), docosahexaenoic acid (DHA) and the like.

Examples of the higher alcohols include linear alcohols such as lauryl alcohol, cetyl alcohol, stearyl alcohol, behenyl alcohol, myristyl alcohol, oleyl alcohol and cetostearyl alcohol, and branched alcohols such as glycerol monostearyl ether (batyl alcohol), 2-decyltetradecinol, lanolin alcohol, cholesterol, phytosterol, hexyldodecanol, isostearyl alcohol and octyldodecanol.

Examples of the synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerol di-2-heptylundecanoate, trimethylolpropane tri-2-ethylhexanoate, trimethylolpropane triisostearate, pentaerythritol tetra-2-ethylhexanoate, glycerol tri-2-ethylhexanoate, trimethylolpropane triisostearate, cetyl 2-ethylhexanoate, 2-ethylhexyl palmitate, glycerol trimyristate, glyceride tri-2-heptylundecanoate, castor oil fatty acid methyl ester, oleyl oleate, acetoglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, triethyl citrate, glycerol trioctanoate, glycerol triisopalmitate, diglyceryl isostearate, diglyceryl diisostearate, diglyceryl triisostearate, (isostearic acid/sebacic acid) ditrimethylolpropane oligoester, ditrimethylolpropane triethylhexanoate, erythrityl triethylhexanoate, pentaerythrityl tetraisostearate and the like.

Examples of the natural ester oils include avocado oil, camellia oil, turtle oil, macadamia nut oil, corn oil, sunflower oil, mink oil, olive oil, rapeseed oil, egg yolk oil, sesame oil, persic oil, wheat germ oil, sasanqua oil, castor oil, linseed oil, safflower oil, grapeseed oil, cotton seed oil, perilla oil, soybean oil, peanut oil, tea seed oil, Japanese nutmeg oil, rice germ oil, tung oil, Japanese tung oil, jojoba oil, germ oil, evening primrose oil and the like.

Examples of the silicone oils include chain-like polysiloxanes such as dimethylpolysiloxane, methylphenylpolysiloxane and methylhydrogenpolysiloxane, cyclic polysiloxanes such as octamethylcyclotetrasiloxane, decamethylcyclopentasiloxane, dodecamethylcyclohexasiloxane and tetrahydrotetramethylcyclotetrasiloxane, and polyoxyethylene polyalkylsiloxanes.

As the oil component, among the components listed above, an ester oil which contains hydroxyl groups, has a hydroxyl value of 40 to 300, and is a liquid at normal temperature is particularly preferred. Further, an oil component having a hydroxyl value of 40 to 100 is more preferred, and an oil component having a hydroxyl value of 40 to 90 is particularly desirable.

Examples of preferred ester oils which have a hydroxyl value of 40 to 300 and are liquid at normal temperature include diisostearyl malate, diglyceryl isostearate, diglyceryl diisostearate, diglyceryl triisostearate, (isostearic acid/sebacic acid) ditrimethylolpropane oligoester, ditrimethylolpropane triethylhexanoate, erythrityl triethylhexanoate, castor oil and the like.

The added oil component may be either a single component or a mixture of two or more components. In the case of a mixture of two or more components, the combination used and the ratio between the components may be selected appropriately in accordance with the intended purpose. Specific examples of preferred mixtures include combinations of an ester oil and a silicone oil, and a combination of an above-mentioned ester oil which has a hydroxyl value of 40 to 300 and is a liquid at normal temperature, and a silicone oil composed of a chain-like polysiloxane is particularly preferred.

The amount added of the oil component may be adjusted appropriately in accordance with factors such as the intended use of the target cosmetic transparent gel preparation.

By including an ester oil which has a hydroxyl value of 40 to 300 and is liquid at normal temperature in an amount that is preferably not less than 20% by mass, more preferably not less than 30% by mass, and still more preferably within a range from 40 to 60% by mass, the cosmetic transparent gel preparation of the present invention is able to exhibit particularly superior effects.

If required, the cosmetic transparent gel preparation of the present invention may also include other components besides the essential components described above, provided these other components do not impair the effects of the present invention, and examples of these other components include humectants, preservatives, antioxidants, ultraviolet absorbers, macromolecules, surfactants, powders, pigments, dyes, alcohols, medicinal agents, solvents, fragrances and the like.

The term "gelling agent" generally refers to a component that, when mixed with a liquid oil, causes gelling and solidification.

The gelling agent of the present invention contains the esterification reaction product according to the present invention, namely the esterification reaction product obtained by reacting glycerol with a dibasic acid of 18 to 28 carbon atoms and a fatty acid of 8 to 28 carbon atoms (excluding dibasic acids), together with 12-hydroxystearic acid.

By mixing the gelling agent of the present invention with the oil component described above, a cosmetic transparent gel preparation having high levels of transparency and hardness and favorable usability can be produced.

As mentioned above, the mass ratio between the components of the gelling agent of the present invention, namely the 12-hydroxystearic acid and the esterification reaction product of the present invention (namely, the mass ratio of 12-hydroxystearic acid: esterification reaction product of the present invention), is preferably within a range from 20:1 to 1:2, more preferably from 10:1 to 1:1, still more preferably from 5:1 to 1:1, and still more preferably from 5:1 to 2:1.

Examples of the humectants include polyethylene glycol, propylene glycol, glycerol, 1,3-butylene glycol, xylitol, sorbitol, maltitol, chondroitin sulfuric acid, hyaluronic acid, mucoitin sulfuric acid, charonin sulfuric acid, atelocollagen, cholesteryl 12-hydroxystearate, sodium lactate, urea, salts of bile acid, salts of dl-pyrrolidonecarboxylic acid, short-chain soluble collagen, diglycerol (EO) PO adducts, extract of chestnut rose, extract of yarrow, extract of melilot and the like.

Examples of the preservatives include ethylparaben, butylparaben and the like.

Examples of the antioxidants include phosphoric acid, citric acid, ascorbic acid, maleic acid, malonic acid, succinic acid, fumaric acid, cephalin, hexametaphosphate, phytic acid, ethylenediaminetetraacetic acid and the like.

Examples of the ultraviolet absorbers include benzoic acid-based ultraviolet absorbers such as para-aminobenzoic acid (hereinafter abbreviated as PABA), glycerol mono PABA ester, N,N-dipropoxy PABA ethyl ester, N,N-diethoxy PABA ethyl ester, N,N-dimethyl PABA ethyl ester, and N,N-dimethyl PABA butyl ester, anthranilic acid-based ultraviolet absorbers such as homomenthyl N-acetylanthranilate, salicylic acid-based ultraviolet absorbers such as amyl salicylate, menthyl salicylate, homomenthyl salicylate, octyl salicylate, phenyl salicylate, benzyl salicylate and p-isopropanolphenyl salicylate, cinnamic acid-based ultraviolet absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate and glyceryl mono-2-ethylhexanoyl-diparamethoxycinnamate, benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, salts of 2-hydroxy-4-methoxybenzophenone-5-sulfonic acid, 4-phenylbenzophenone, 2-ethylhexyl 4'-phenylbenzophenone-2-carboxylate, 2-hydroxy-4-n-octoxybenzophenone and 4-hydroxy-3-carboxybenzophenone, as well as 3-(4'-methylbenzylidene)-d,l-camphor, 3-benzylidene-d,l-camphor, urocanic acid, ethyl urocanate, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane, 5-(3,3-dimethyl-2-norbornylidene)-3-pentan-2-one, 2,4,6-trianilino-p-(carbo-2'-ethylhexyl-1'-oxy)-1,3,5-triazine and the like.

Examples of the macromolecules include naturally occurring water-soluble macromolecules, semi-synthetic water-soluble macromolecules, synthetic water-soluble macromolecules, inorganic water-soluble macromolecules and the like.

Specific examples of the naturally occurring water-soluble macromolecules include plant-based macromolecules such as gum arabic, tragacanth gum, galactan, guar gum, carob gum, karaya gum, carrageenin, locust bean gum, tamarind gum, pectin, agar, quince seed (*cydonia oblonga*), algae colloid (algae extract) and starch (from rice, corn, potato and wheat), microbial macromolecules such as xanthan gum, dextran, succinoglucan and pullulan, and animal-based macromolecules such as collagen, casein, albumin and gelatin.

Further, specific examples of the semi-synthetic water-soluble macromolecules include starch-based macromolecules such as carboxymethyl starch and methylhydroxypropyl starch, cellulose-based macromolecules such as methylcellulose, nitrocellulose, methylhydroxypropylcellulose, sodium cellulose sulfate, hydroxypropylcellulose, carboxymethylcellulose, sodium carboxymethylcellulose, crystalline cellulose and cellulose powder, and alginic acid-based macromolecules such as sodium alginate and propylene glycol alginate.

Furthermore, specific examples of the synthetic water-soluble macromolecules include vinyl-based macromolecules such as polyvinyl alcohol, polyvinyl methyl ether, polyvinylpyrrolidone and carboxyvinyl polymers (carbopol), polyoxyethylene-based macromolecules such as polyethylene glycols 20,000, 40,000 and 60,000, polyoxyethylene-polyoxypropylene copolymer-based macromolecules, acrylic-based macromolecules such as sodium polyacrylate, polyethyl acrylate and polyacrylamide, polyethyleneimine and cationic polymers.

Furthermore, specific examples of the inorganic water-soluble macromolecules include bentonite, AlMg silicate (veegum), laponite, hectorite, silicic acid anhydride and the like.

Examples of the surfactants include synthetic surfactants or naturally occurring surfactants such as anionic surfactants, cationic surfactants, amphoteric surfactants, lipophilic nonionic surfactants and hydrophilic nonionic surfactants.

Specific examples of the anionic surfactants include fatty acid soaps such as soap bases, sodium laurate and sodium palmitate; salts of higher alkyl sulfate esters such as sodium lauryl sulfate and potassium lauryl sulfate; salts of alkyl ether sulfate esters such as the triethanolamine salt of POE lauryl sulfate and sodium POE lauryl sulfate; N-acylsarcosine salts such as sodium lauroyl sarcosine; salts of higher fatty acid amido-sulfonic acids such as sodium N-myristoyl-N-methyl taurate, sodium coconut oil fatty acid methyl tauride and sodium laurylmethyl tauride; salts of phosphate esters such as sodium POE oleyl ether phosphate; salts of sulfosuccinic acids such as sodium di-2-ethylhexyl sulfosuccinate, sodium monolauroyl monoethanolamide polyoxyethylene sulfosuccinate and sodium lauryl polypropylene glycol sulfosuccinate; salts of alkylbenzenesulfonic acids such as sodium linear dodecylbenzenesulfonate, and the triethanolamine salt of linear dodecylbenzenesulfonate; salts of N-acylglutamic acids such as monosodium N-lauroyl glutamate, disodium N-stearoyl glutamate and monosodium N-myristoyl-L- glutamate; salts of higher fatty acid ester sulfates such as the sodium salt of hardened coconut oil fatty acid glycerol sulfate; sulfated oils such as Turkey red oil; as well as POE alkyl ether carboxylic acids, POE alkylaryl ether carboxylates, salts of α-olefin sulfonic acids, salts of higher fatty acid ester sulfonic acids, salts of secondary alcohol sulfate esters, salts of higher fatty acid alkylol amide sulfate esters, sodium lauroyl monoethanolamide succinate, the di-triethanolamine salt of N-palmitoylaspartic acid, sodium caseinate and the like.

Further, specific examples of the cationic surfactants include alkyltrimethylammonium salts such as stearyltrimethylammonium chloride and lauryltrimethylammonium chloride, dialkyldimethylammonium salts such as distearyldimethylammonium chloride, alkylpyridinium salts such as poly(N,N'-dimethyl-3,5-methylenepiperidinium) chloride and cetylpyridinium chloride, alkyl quaternary ammonium salts, alkyldimethylbenzylammonium salts, alkylisoquinolinium salts, dialkylmorphonium salts, POE alkylamines, alkylamine salts, polyamine fatty acid derivatives, amyl alcohol fatty acid derivatives, benzalkonium chloride, benzethonium chloride, and organically modified clay minerals such as organically modified montmorillonite.

Specific examples of the amphoteric surfactants include imidazoline-based amphoteric surfactants such as sodium 2-undecyl-N,N,N-(hydroxyethylcarboxymethyl)-2-imidazoline and disodium 2-cocoyl-2-imidazolinium hydroxide-1-carboxyethyloxy; and betaine-based surfactants such as 2-heptadecyl-N-carboxymethyl-N-hydroxyethylimidazolinium betaine, lauryldimethylaminoacetic acid betaine, alkyl betaines, amide betaines and sulfobetaines.

Specific examples of the lipophilic nonionic surfactants include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; glycerol fatty acid esters such as glycerol mono-cottonseed oil fatty acid ester, glycerol monoerucate, glycerol sesquioleate, glycerol monostearate, glycerol α,α'-oleate pyroglutamate, glycerol monostearate and glycerol monooleate; polyglycerol fatty acid esters such as diglyceryl monoisostearate, diglyceryl diisostearate, diglyceryl condensed ricinoleate and tetraglyceryl condensed ricinoleate; propylene glycol fatty acid esters such as propylene glycol monostearate; hardened castor oil derivatives; glycerol alkyl ethers and the like.

Further, specific examples of the hydrophilic nonionic surfactants include POE sorbitan fatty acid esters such as POE sorbitan monooleate, POE sorbitan monostearate, and POE sorbitan tetraoleate; POE sorbitol fatty acid esters such as POE sorbitol monolaurate, POE sorbitol monooleate, POE sorbitol pentaoleate and POE sorbitol monostearate; POE glycerol fatty acid esters such as POE glycerol monostearate, POE glycerol monoisostearate and POE glycerol triisostearate; POE fatty acid esters such as POE monooleate, POE distearate, POE dioleate and ethylene glycol distearate; POE alkyl ethers such as POE lauryl ether, POE oleyl ether, POE stearyl ether, POE behenyl ether, POE 2-octyldodecyl ether and POE cholestanol ether; Pluronics such as Pluronic; POE-POP alkyl ethers such as POE-POP cetyl ether, POE-POP 2-decyltetradecyl ether, POE-POP monobutyl ether, POE-POP hydrogenated lanolin ether and POE-POP glycerol ether; tetra-POE-tetra-POP ethylenediamine condensates such as Tetronic; POE castor oil/hardened castor oil derivatives such as POE castor oil, POE hardened castor oil, POE hardened castor oil monoisostearate, POE hardened castor oil triisostearate, POE hardened castor oil monopyroglutamate monoisostearate diester and POE hardened castor oil maleate; POE beeswax lanolin derivatives such as POE sorbitol beeswax; alkanolamides such as coconut oil fatty acid diethanolamide, lauric acid monoethanolamide and fatty acid isopropanolamides; POE propylene glycol fatty acid esters, POE alkylamines, POE fatty acid amides, sucrose fatty acid esters, POE nonylphenyl formaldehyde condensates, alkylethoxydimethylamine oxides, trioleyl phosphoric acid; polyglycerol fatty acid esters such as polyglyceryl monolaurate, polyglyceryl monostearate, polyglyceryl monooleate, polyglyceryl distearate and polyglyceryl dioleate; and modified silicones such as copolymers of methylpolysiloxane, cetylmethylpolysiloxane and poly(oxyethylene-oxypropylene)methylpolysiloxane.

Specific examples of the naturally occurring surfactants include lecithins such as soybean phospholipid, hydrogenated soybean phospholipid, egg yolk phospholipid and hydrogenated egg yolk phospholipid, soybean saponin and the like.

Examples of the powders, pigments and dyes include inorganic powders such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal salts of tungstic acid, magnesium, silica, zeolite, barium sulfate, calcined calcium sulfate (calcined gypsum), calcium phosphate, fluorapatite, hydroxyapatite, ceramic powder, metallic soaps (such as zinc myristate, calcium palmitate and aluminum stearate) and boron nitride; organic powders such as polyamide resin powder (nylon powder), polyethylene powder, poly(methyl methacrylate) powder, polystyrene powder, powder of a copolymer resin of styrene and acrylic acid, benzoguanamine resin powder, poly(ethylene tetrafluoride) powder and cellulose powder; inorganic white pigments such as titanium dioxide and zinc oxide; inorganic red pigments such as iron oxide (red iron oxide) and iron titanate; inorganic brown pigments such as iron oxide; inorganic yellow pigments such as yellow iron oxide and yellow ocher; inorganic black pigments such as black iron oxide, carbon black and titanium oxide of a low degree of oxidation; inorganic purple pigments such as mango violet and cobalt violet; inorganic green pigments such as chromium oxide, chromium hydroxide and cobalt titanate; inorganic blue pigments such as ultramarine blue and Prussian blue; pearl pigments such as titanium oxide-coated mica, titanium oxide-coated bismuth oxychloride, titanium oxide-coated talc, colored titanium oxide-coated mica, bismuth oxychloride and fish scale guanine; metal powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404; organic pigments including zirconium lakes, barium lakes or aluminum lakes or the like, such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1; and natural colorants such as chlorophyll, β-carotene and the like.

Examples of the alcohols include lower alcohols and polyhydric alcohols.

Specific examples of the lower alcohols include methanol, ethanol, propanol, isopropanol, isobutyl alcohol, t-butyl alcohol and the like.

Further, specific examples of the polyhydric alcohols include dihydric alcohols such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol; trihydric alcohols such as glycerol, trimethylolpropane and 1,2,6-hexanetriol; tetrahydric alcohols such as pentaerythritol; pentahydric alcohols such as xylitol; hexahydric alcohols such as sorbitol and mannitol; polymers of polyhydric alcohols such as diethylene glycol, dipropylene glycol, triethylene glycol, polypropylene glycol, tetraethylene glycol, diglycerol, polyethylene glycol, triglycerol, tetraglycerol and polyglycerol; alkyl ethers of dihydric alcohols such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether and ethylene glycol dibutyl ether; alkyl ethers of dihydric alcohols such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether; ether esters of dihydric alcohols such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate and propylene glycol monophenyl ether acetate; glycerol monoalkyl ethers such as chimyl-alcohol, selachyl alcohol and batyl alcohol; sugar alcohols such as sorbitol, maltitol, maltotriose, mannitol, sucrose, erythritol, glucose, fructose, sugars obtained by amylolysis, maltose, xylitose and alcohols obtained by reducing sugars obtained by amylolysis; as well as glysolid, tetrahydrofurfuryl alcohol, POE tetrahydrofurfuryl alcohol, POP butyl ether, POP-POE butyl ether, tripolyoxypropylene glycerol ether, POP glycerol ether, POP glycerol ether phosphoric acid, POP-POE pentaerythritol ether and the like.

The other components added may be either a single component or a mixture of two or more components. In the case of a mixture of two or more components, the combination used and the ratio between the compounds may be selected appropriately in accordance with the intended purpose.

Examples of product formulations for the cosmetic transparent gel preparation of the present invention include makeup cosmetics such as lipstick, lip gloss, lip cream and eye shadow, and hair cosmetics such as hair stick and pomade. Of these, in terms of achieving particularly superior effects, the present invention is particularly suited to stick-type transparent solid cosmetic preparations.

The cosmetic transparent gel preparation of the present invention can be produced using conventional methods. In a sample method, the esterification reaction product obtained by reacting glycerol, the dibasic acid of 18 to 28 carbon atoms and the fatty acid of 8 to 28 carbon atoms (excluding dibasic acids) is blended with the 12-hydroxystearic acid, the oil component and any other components that are added according to need, the resulting mixture is then heated and melted to achieve a homogenous mixture, and the mixture is then cooled and molded into the desired form.

During blending, the gelling agent of the present invention, namely the mixture of the 12-hydroxystearic acid and the esterification reaction product of the present invention, is preferably added to the oil component.

There are no particular limitations on the temperature during the heating and melting step, and the temperature may be adjusted depending on the blend components, but normally a temperature of 90° C. or lower is sufficient, and a temperature of approximately 75 to 85° C. is preferred. In the present invention, because of the combination of components used, even though heating is not performed at a high temperature of 95° C. or higher, each of the blend components is able to be melted, and therefore deterioration of the oil component in particular can be prevented, and a high-quality cosmetic preparation can be produced.

The hardness of the cosmetic transparent gel preparation of the present invention can be adjusted by altering the blend amount of the gelling agent. The hardness may be adjusted appropriately in accordance with factors such as the intended application of the target cosmetic transparent gel preparation. For example, in the case where, as described above, a mixture of 12-hydroxystearic acid and the esterification reaction product of the present invention is used as the gelling agent, then usually the blend amount of this mixture is preferably within a range from 5 to 30% by mass, and more preferably from 7 to 25% by mass, based on the total mass of all the blended components.

Specifically, using the "rupture strength" described in the following examples as an example, if the blend amount of the above mixture is 10% by mass or greater, then a product having a rupture strength of at least 140 is obtained, if the blend amount of the mixture is 12% by mass or greater, then the rupture strength of the product is at least 175, if the blend amount of the mixture is 15% by mass or greater, then the rupture strength of the product is at least 200, and if the blend amount of the mixture is 20% by mass or greater, then the rupture strength of the product is at least 300. Further, even following storage of the cosmetic transparent gel preparation of the present invention at approximately room temperature for approximately one month, the high level of hardness can be maintained.

The cosmetic transparent gel preparation of the present invention addresses the usability and transparency problems associated with conventional transparent cosmetic preparations such as poor spreadability upon application, an unsatisfactory finish, and deterioration in the transparency over time.

Moreover, the cosmetic transparent gel preparation of the present invention has a high level of hardness and excellent quality for a cosmetic gel preparation.

EXAMPLES

The present invention is described in more detail below based on a series of specific examples. However, the present invention is in no way limited by these examples.

Unless stated otherwise, the blend amounts the various components listed below are "% by mass".

Examples 1 to 12, Comparative Examples 1 to 8

<Production of Cosmetic Transparent Gel Preparations>

Using the blend ratios shown in Tables 1 to 5, a series of cosmetic transparent gel preparations were prepared by adding a gelling agent (a mixture of 12-hydroxystearic acid and an esterification reaction product of the present invention) to an oil component, heating the resulting mixture at 80° C. to melt the components and generate a homogenous mixture, pouring the resulting mixture into a mold, and then performing molding into a cylindrical shape with a diameter of 12 mm by cooling to 0° C. However, in the case of comparative example 2 only, the cosmetic transparent gel preparation was obtained in a similar manner to that described above, with the exception that the oil component and dextrin fatty acid ester were first melted by heating to 95° C., and the 12-hydroxystearic acid was then added. In the tables, "-" means either no addition or not applicable.

In Tables 1 to 5, the raw materials denoted *1 to *7 refer to the commercially available products listed below.

*1: product name: NOMCORT SG, manufactured by Nisshin Oillio Group
*2: product name: NOMCORT HK-G, manufactured by Nisshin Oillio Group
*3: product name: RHEOPEARL KL, manufactured by Chiba Flour Milling Co., Ltd.
*4: product name: COSMOL 222 (hydroxyl value: 80), manufactured by Nisshin Oillio Group
*5: product name: KF56 (hydroxyl value: 0), manufactured by Shin-Etsu Chemical Co., Ltd.
*6: product name: COSMOL 43 (hydroxyl value: 47), manufactured by Nisshin Oillio Group
*7: product name: SALACOS 5418 (hydroxyl value: 1), manufactured by Nisshin Oillio Group The raw materials of *4 to *7 are all liquids at normal temperature.

Further, "glyceryl (behenate/isostearate/eicosanedioate)" represents "an esterification reaction product obtained by reacting glycerol, behenic acid, isostearic acid and eicosanedioic acid", and "glyceryl (behenate/eicosanedioate)" represents "an esterification reaction product obtained by reacting glycerol, behenic acid and eicosanedioic acid".

<Evaluation of Quality of Cosmetic Transparent Gel Preparations>

Each of the obtained cosmetic transparent gel preparations was stored for one month at 25° C., and then evaluated for rupture strength, hardness, transparency, and the state obtained following application. The results of the evaluations are shown in Tables 1 to 5. Evaluations of the various properties were performed in accordance with the methods and evaluation criteria described below.

(Rupture Strength, Hardness)

The cosmetic transparent gel preparation was left to stand for one hour at 20° C., and then using a rheometer (manufactured by Fudoh Kogyo Co., Ltd.), a plunger with a diameter of 3 mm was used to press the sample at a mounting rate of 60 mm/minute, and the maximum stress value was measured and recorded as the rupture strength. The criterion for evaluating the hardness is described below. Namely, evaluation was conducted on the basis of the following relational formula, wherein the standard comparative example was deemed to be comparative example 1 for examples 1 to 8, comparative example 5 for examples 9-11, comparative example 6 for example 12, and comparative example 8 for example 13 respectively. In the following formula, X represents the hardness of the example, or a comparative example other than the standard comparative example, and Y represents the hardness of the standard comparative example.

A: the rupture strength is higher than that of the standard comparative example ($1.2<X/Y$)

B: the rupture strength is similar to that of the standard comparative example ($0.8 \leq X/Y \leq 1.2$)

C: the rupture strength is lower than that of the standard comparative example ($0.5 \leq X/Y \leq 0.8$)

D: the rupture strength is much lower than that of the standard comparative example ($X/Y < 0.5$)

(Transparency)

The transparency was evaluated based on the ease of readability of a hiragana character "a" (size of character: 1 cm square) positioned 0.5 cm behind a glass bottle containing the sample, when viewed through the bottle. The evaluation criteria for the transparency are listed below.

A: the character can be read clearly

B: the character appears clouded, but can be read

C: the existence of the character is apparent, but the character is unreadable

D: the existence of the character cannot be confirmed (Usability)

The sample was poured into a mold to prepare a stick-type cosmetic preparation, and following application of the preparation to the lips, the degree of disintegration at the application surface of the stick was evaluated. The evaluation criteria are listed below.

A: no surface disintegration

B: almost no surface disintegration

C: slight surface disintegration

D: very noticeable surface disintegration

TABLE 1

Gelling agent: 15% by mass, standard comparative example: comparative example 1

| | | Example | | | | | | | |
|---|---|---|---|---|---|---|---|---|---|
| | | 1 | 2 | 3 | 4 | 5 | 6 | 7 | 8 |
| Gelling agent | 12-hydroxystearic acid | 14 | 10 | 10 | 10 | 10 | 10 | 10 | 10 |
| | Glyceryl (behenate/isostearate/eicosanedioate) (*1) | 1 | 5 | 5 | 5 | — | 5 | 5 | 5 |
| | Glyceryl (behenate/eicosanedioate) (*2) | — | — | — | — | 5 | — | — | — |
| | Dextrin palmitate (*3) | — | — | — | — | — | — | — | — |
| | 12-hydroxystearic acid:esterification reaction product (mass ratio) | 14:1 | 2:1 | 2:1 | 2:1 | 2:1 | 2:1 | 2:1 | 2:1 |
| Oil component | Diisostearyl malate (*4) | 51 | 51 | 57 | — | 51 | 43 | — | 23 |
| | Methylphenylpolysiloxane (*5) | 34 | 34 | 28 | 29 | 34 | 42 | — | 22 |
| | Diglyceryl triisostearate (*6) | — | — | — | 56 | — | — | — | — |
| | Pentaerythrityl tetraisostearate (*7) | — | — | — | — | — | — | 85 | 40 |
| Evaluation results | Hardness | B | B | B | B | A | B | B | B |
| | Rupture strength | 239 | 245 | 212 | 217 | 465 | 248 | 244 | 248 |
| | Transparency | B | A | A | A | B | A | B | B |
| | Usability | B | A | A | A | A | A | B | A |

TABLE 2

Gelling agent: 15% by mass, standard comparative example: comparative example 1

| | | Comparative example | | | |
|---|---|---|---|---|---|
| | | 1 | 2 | 3 | 4 |
| Gelling agent | 12-hydroxystearic acid | 15 | 10 | — | — |
| | Glyceryl (behenate/isostearate/eicosanedioate) (*1) | — | — | 15 | — |
| | Glyceryl (behenate/eicosanedioate) (*2) | — | — | — | 15 |
| | Dextrin palmitate (*3) | — | 5 | — | — |
| | 12-hydroxystearic acid:esterification reaction product (mass ratio) | — | — | — | — |
| Oil component | Diisostearyl malate (*4) | 51 | 51 | 51 | 51 |
| | Methylphenylpolysiloxane (*5) | 34 | 34 | 34 | 34 |
| | Diglyceryl triisostearate (*6) | — | — | — | — |
| | Pentaerythrityl tetraisostearate (*7) | — | — | — | — |
| Evaluation results | Hardness | B | D | D | B |
| | Rupture strength | 233 | could not be molded | 71 | 233 |
| | Transparency | C | A | D | D |
| | Usability | D | D | D | D |

TABLE 3

Gelling agent: 20% by mass, standard comparative example: comparative example 5

| | | Example | | | Comparative example |
|---|---|---|---|---|---|
| | | 9 | 10 | 11 | 5 |
| Gelling agent | 12-hydroxystearic acid | 18 | 15 | 10 | 20 |
| | Glyceryl (behenate/isostearate/eicosanedioate) (*1) | 2 | 5 | 10 | — |
| | Glyceryl (behenate/eicosanedioate) (*2) | — | — | — | — |
| | Dextrin palmitate (*3) | — | — | — | — |
| | 12-hydroxystearic acid:esterification reaction product (mass ratio) | 9:1 | 3:1 | 1:1 | — |
| Oil component | Diisostearyl malate (*4) | 48 | 48 | 48 | 48 |
| | Methylphenyl-polysiloxane (*5) | 32 | 32 | 32 | 32 |
| | Diglyceryl triisostearate (*6) | — | — | — | — |
| | Pentaerythrityl tetraisostearate (*7) | — | — | — | — |
| Evaluation results | Hardness | A | A | A | B |
| | Rupture strength | 352 | 371 | 341 | 232 |
| | Transparency | B | B | B | C |
| | Usability | A | A | A | D |

TABLE 4

Gelling agent: 12% by mass, standard comparative example: comparative example 6

| | | Example 12 | Comparative example 6 |
|---|---|---|---|
| Gelling agent | 12-hydroxystearic acid | 10 | 12 |
| | Glyceryl (behenate/isostearate/eicosanedioate) (*1) | 2 | — |
| | Glyceryl (behenate/eicosanedioate) (*2) | — | — |
| | Dextrin palmitate (*3) | — | — |
| | 12-hydroxystearic acid:esterification reaction product (mass ratio) | 5:1 | — |
| Oil component | Diisostearyl malate (*4) | 53 | 53 |
| | Methylphenylpolysiloxane (*5) | 35 | 35 |
| | Diglyceryl triisostearate (*6) | — | — |
| | Pentaerythrityl tetraisostearate (*7) | — | — |
| Evaluation results | Hardness | B | D |
| | Rupture strength | 185 | 168 |
| | Transparency | A | B |
| | Usability | A | D |

TABLE 5

Gelling agent: 10% by mass, standard comparative example: comparative example 8

| | | Example 13 | Comparative example 7 | Comparative example 8 |
|---|---|---|---|---|
| Gelling agent | 12-hydroxystearic acid | 8 | — | 10 |
| | Glyceryl (behenate/isostearate/eicosanedioate) (*1) | 2 | — | — |
| | Glyceryl (behenate/eicosanedioate) (*2) | — | 10 | — |
| | Dextrin palmitate (*3) | — | — | — |
| | 12-hydroxystearic acid:esterification reaction product (mass ratio) | 4:1 | — | — |
| Oil component | Diisostearyl malate (*4) | 54 | 54 | 54 |
| | Methylphenylpolysiloxane (*5) | 36 | 36 | 36 |
| | Diglyceryl triisostearate (*6) | — | — | — |
| | Pentaerythrityl tetraisostearate (*7) | — | — | — |
| Evaluation results | Hardness | B | B | B |
| | Rupture strength | 147 | 127 | 130 |
| | Transparency | A | D | B |
| | Usability | A | D | D |

INDUSTRIAL APPLICABILITY

The present invention can be used in fields relating to all manner of cosmetic preparations.

The invention claimed is:

1. A cosmetic transparent gel preparation, comprising
   an esterification reaction product obtained by reacting glycerol with a dibasic acid and a fatty acid,
   12-hydroxystearic acid, and
   an oil component,
   wherein the dibasic acid is at least one dicarboxylic acid selected from the group consisting of octadecanedioic acid, nonadecanedioic acid and eicosanedioic acid,
   the fatty acid is at least one fatty acid selected from the group consisting of caprylic acid, capric acid, lauric acid, myristic acid, palmitic acid, stearic acid, behenic acid, oleic acid, ricinoleic acid, palmitoleic acid, isooctanoic acid, isononanoic acid, isopalmitic acid, isostearic acid, isoeicosanoic acid, cerotic acid, montanic acid and melissic acid, the oil component is at least one selected from the group consisting of liquid oils and fats, solid oils and fats, waxes, hydrocarbon oils, higher fatty acids, higher alcohols, synthetic ester oils, natural ester oils and silicone oils, and a mass ratio between the 12-hydroxystearic acid and the esterification reaction products is within a range of from 9:1 to 1:2.

2. The cosmetic transparent gel preparation according to claim 1, comprising 4 to 20% by mass of the 12-hydroxystearic acid, and 1 to 15% by mass of the esterification reaction product.

3. The cosmetic transparent gel preparation according to claim 1, wherein the mass ratio between the 12-hydroxystearic acid and the esterification reaction product is within a range from 5:1 to 1:1.

4. The cosmetic transparent gel preparation according to claim 1, wherein the mass ratio between the 12-hydroxystearic acid and the esterification reaction product is within a range from 5:1 to 2:1.

5. The cosmetic transparent gel preparation according to claim 1, wherein the dibasic acid is eicosanedioic acid, and the fatty acid is at least one saturated fatty acid selected from the group consisting of beheic acid and isostearic acid.

6. The cosmetic transparent gel preparation according to claim 1, wherein the esterification product has a hydroxyl value of 40 or less.

7. The cosmetic transparent gel preparation according to claim 1, comprising, as the oil component, not less than 20% by mass of an ester oil that has a hydroxyl value of 40 to 300 and is a liquid at normal temperature.

8. The cosmetic transparent gel preparation according to claim 7, wherein the ester oil which is a liquid at normal temperature is at least one ester oil selected from the group consisting of diisostearyl malate, diglyceryl isostearate, diglyceryl diisostearate, diglyceryl triisostearate, (isostearic acid/sebacic acid) ditrimethylolpropane oligoester, ditrimethylolpropane triethylhexanoate, erythrityl triethylhexanoate and castor oil.

9. The cosmetic transparent gel preparation according to claim 1, wherein the oil component is at least one selected from the group consisting of diisostearyl malate, diglyceryl triisostearate, pentaerythrityl tetraisostearate, and methylphenylpolysiloxane.

10. The cosmetic transparent gel preparation according to claim 1, wherein an amount of a mixture of 12-hydroxystearic acid and the esterification reaction product is 5 to 30% by mass.

11. A gelling agent, comprising an esterification reaction product obtained by reacting glycerol with a dibasic acid and a fatty acid, and 12-hydroxystearic acid, wherein the dibasic acid is at least one dicarboxylic acid selected from the group consisting of octadecanedioic acid, nonadecanedioic acid and eicosanedioic acid, the fatty acid is at least one fatty acid selected from the group consisting of caprylic acid, capric acid, lauric acid, myristic acid, palmitic acid, stearic acid, behenic acid, oleic acid, ricinoleic acid, palmitoleic acid, isooctanoic acid, isononanoic acid, isopalmitic acid, isostearic acid, isoeicosanoic acid, cerotic acid, montanic acid and melissic acid, and a mass ratio between the 12-hydroxystearic acid and the esterification reaction products is within a range of from 9:1 to 1:2.

12. The gelling agent according to claim 11, wherein the mass ratio between the 12-hydroxystearic acid and the esterification reaction product is within a range from 5:1 to 1:1.

13. The gelling agent according to claim 11, wherein the mass ratio between the 12-hydroxystearic acid and the esterification reaction product is within a range from 5:1 to 2:1.

14. A cosmetic transparent gel preparation, comprising the gelling agent according to claim 11, and an oil component, wherein the oil component is at least one selected from the group consisting of liquid oils and fats, solid oils and fats, waxes, hydrocarbon oils, higher fatty acids, higher alcohols, synthetic ester oils, natural ester oils and silicone oils.

15. The cosmetic transparent gel preparation according to claim 14, wherein an amount of the gelling agent is 5 to 30% by mass.

* * * * *